Figure 1:
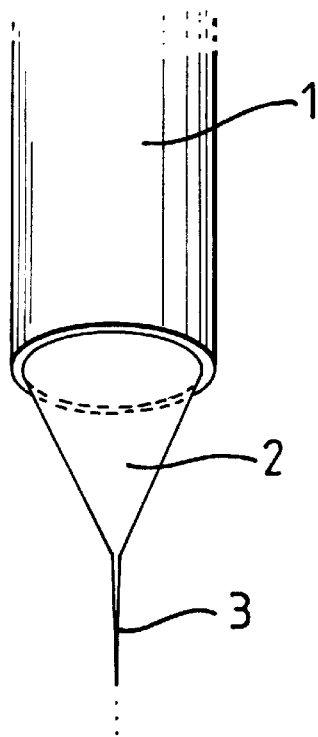
Figure 2:
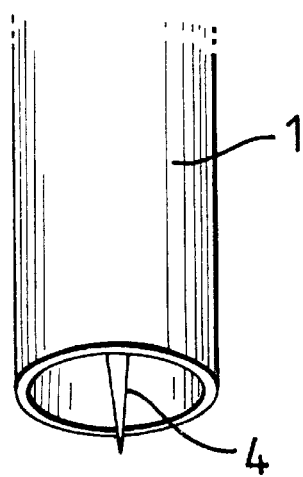
Figure 3:
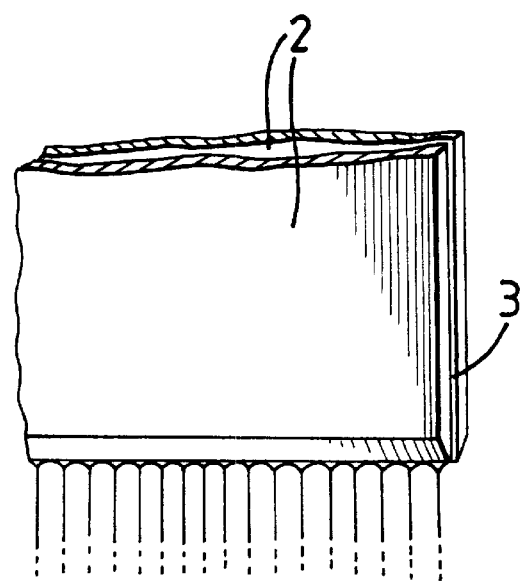
Figure 7:
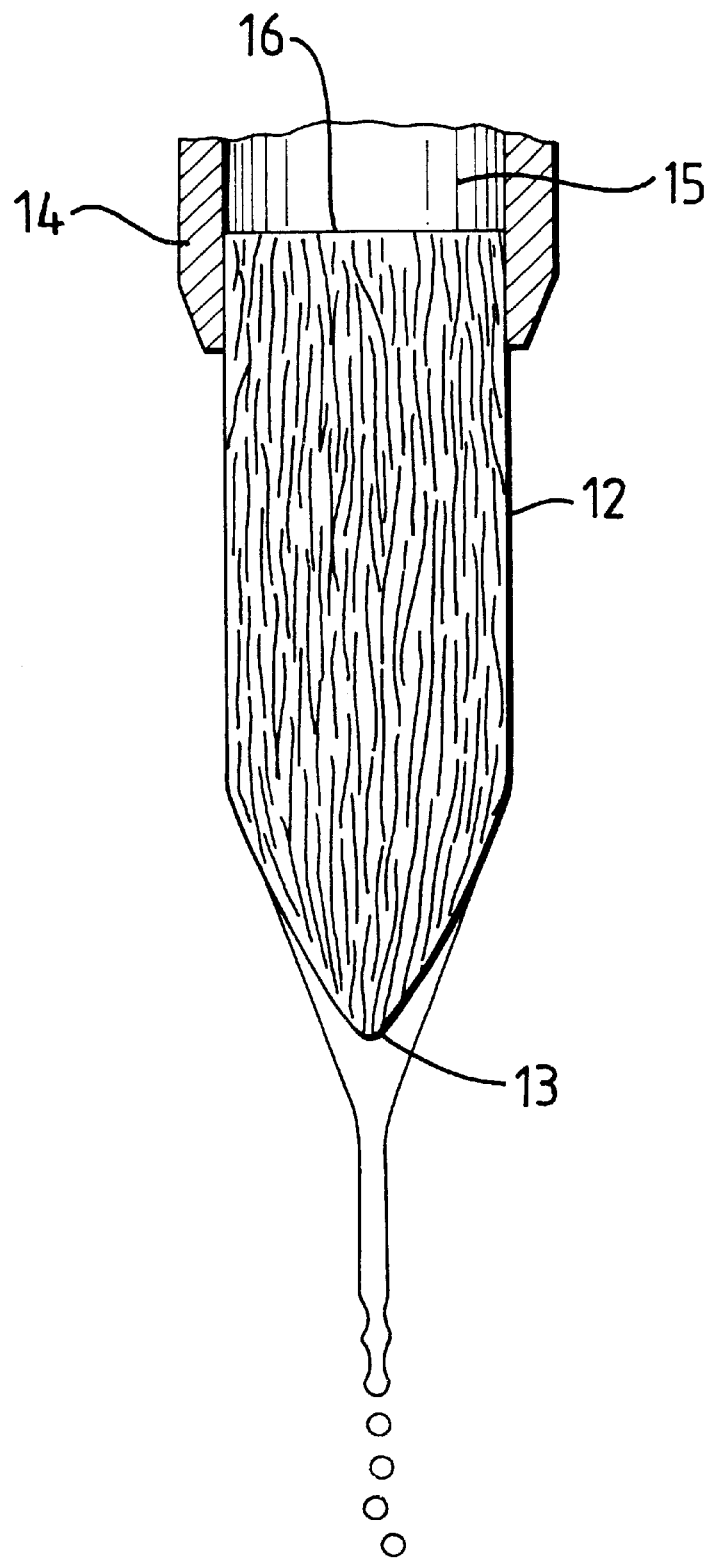

United States Patent
Coffee

[11] Patent Number: 6,068,199
[45] Date of Patent: *May 30, 2000

[54] DISPENSING DEVICE

[75] Inventor: Ronald Alan Coffee, Haslemere, United Kingdom

[73] Assignee: Electrosols, Ltd., Surrey, United Kingdom

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/833,875

[22] Filed: Apr. 10, 1997

Related U.S. Application Data

[63] Continuation of application No. 08/456,606, Jun. 1, 1995, abandoned, which is a continuation of application No. PCT/EP95/01163, Mar. 28, 1995.

[30] Foreign Application Priority Data

Mar. 29, 1994 [GB] United Kingdom .................... 9406171

[51] Int. Cl.[7] .................................................. A01G 15/00

[52] U.S. Cl. .............................. 239/3; 239/690; 239/696; 239/706; 128/203.12

[58] Field of Search ..................................... 239/690, 695, 239/696, 704, 708, 3, 706; 361/227, 228; 128/200.14, 203.12, 204.13, 204.21

[56] References Cited

U.S. PATENT DOCUMENTS

| | | |
|---|---|---|
| 2,723,646 | 11/1955 | Ransburg . |
| 2,945,443 | 7/1960 | Aver et al. . |
| 3,096,762 | 7/1963 | Winchell ................................ 128/190 |
| 3,131,131 | 4/1964 | Wehner . |
| 3,232,292 | 2/1966 | Schaefer ................................ 128/172 |
| 3,456,646 | 7/1969 | Phillips et al. ......................... 128/173 |
| 3,837,573 | 9/1974 | Wagner .................................... 239/15 |
| 3,897,905 | 8/1975 | Tadewald ................................ 239/15 |
| 3,930,061 | 12/1975 | Scharfenberger ....................... 427/27 |
| 3,958,959 | 5/1976 | Cohen et al. ............................. 55/10 |
| 4,073,002 | 2/1978 | Sickles et al. ......................... 361/227 |
| 4,150,644 | 4/1979 | Masaki et al. ......................... 123/119 |

(List continued on next page.)

FOREIGN PATENT DOCUMENTS

| | | |
|---|---|---|
| 0029301A1 | 5/1981 | European Pat. Off. . |
| 0 120 633 A2 | 10/1984 | European Pat. Off. . |
| 0 102 713 B1 | 9/1987 | European Pat. Off. . |
| 0234842 | 9/1987 | European Pat. Off. . |
| 0 243 031 A1 | 10/1987 | European Pat. Off. . |
| 0250164A3 | 12/1987 | European Pat. Off. . |
| 0523963A1 | 7/1992 | European Pat. Off. . |
| 0523962A1 | 1/1993 | European Pat. Off. . |
| 523964A1 | 1/1993 | European Pat. Off. . |

(List continued on next page.)

OTHER PUBLICATIONS

Article entitled: *Charging Liquid Spray by Electrostatic Induction* authored by: S. E. Law and H. D. Bowen; taken from Transactions of the ASAE; pp. 501–506; dated 1966.

Article entitled: Electro–osmosis Controls Fluid in Novel Transducer Concept by Product Engineering, dated Jul. 4, 1970 authored by: Ray Lewis, Cleveland; pp. 71–72.

Article entitled: Electrodynamic Crop Spraying, dated 1981; authored by: R. A. Coffee; Reprinted from Outlook on Agriculture vol. 10, No. 7, 1981; includes excerpt pp. 350–356.

*Primary Examiner*—Lesley D. Morris
*Assistant Examiner*—Lisa Ann Douglas
*Attorney, Agent, or Firm*—Cobrin & Gittes

[57] ABSTRACT

A device for dispensing a comminuted liquid to the upper respiratory tract, which comprises an electrohydrodynamic comminution device and a supplier of a liquid to the comminution device. And a device for comminuting a liquid, the comminution site of which is provided by fibers projecting from an end surface or edge, the edge or surface being composed substantially of fibers.

14 Claims, 3 Drawing Sheets

U.S. PATENT DOCUMENTS

| | | | |
|---|---|---|---|
| 4,186,886 | 2/1980 | Sickles | 239/691 |
| 4,198,781 | 4/1980 | Dykes . | |
| 4,203,398 | 5/1980 | Maruoka | 123/119 |
| 4,266,721 | 5/1981 | Sickles | 239/3 |
| 4,356,528 | 10/1982 | Coffee | 361/226 |
| 4,380,786 | 4/1983 | Kelly . | |
| 4,439,980 | 4/1984 | Biblarz et al. | 60/39.06 |
| 4,467,961 | 8/1984 | Coffee et al. | 239/1 |
| 4,476,515 | 10/1984 | Coffee | 361/226 |
| 4,508,265 | 4/1985 | Jido | 239/3 |
| 4,509,694 | 4/1985 | Inculet et al. | 239/697 |
| 4,549,243 | 10/1985 | Owen et al. | 361/228 |
| 4,659,012 | 4/1987 | Coffee | 239/3 |
| 4,671,269 | 6/1987 | Wilp | 128/202.25 |
| 4,703,891 | 11/1987 | Jackson et al. . | |
| 4,735,364 | 4/1988 | Marchant | 239/690.1 |
| 4,748,043 | 5/1988 | Seaver et al. | 427/30 |
| 4,749,125 | 6/1988 | Escallon et al. | 239/3 |
| 4,776,515 | 10/1988 | Michalchik | 239/3 |
| 4,788,016 | 11/1988 | Colclough et al. | 264/10 |
| 4,801,086 | 1/1989 | Noakes | 239/3 |
| 4,830,872 | 5/1989 | Grenfell . | |
| 4,846,407 | 7/1989 | Coffee et al. | 239/690 |
| 4,962,885 | 10/1990 | Coffee | 239/3 |
| 4,979,680 | 12/1990 | Bauch et al. | 239/692 |
| 5,044,564 | 9/1991 | Sickles | 239/690.1 |
| 5,086,972 | 2/1992 | Chang et al. | 239/3 |
| 5,115,971 | 5/1992 | Greenspan et al. . | |
| 5,180,288 | 1/1993 | Richter et al. . | |
| 5,222,663 | 6/1993 | Noakes et al. | 239/3 |
| 5,267,555 | 12/1993 | Pajalich | 128/200.14 |
| 5,381,789 | 1/1995 | Marquardt | 128/202.25 |
| 5,402,945 | 4/1995 | Swanson . | |
| 5,409,162 | 4/1995 | Sickles | 239/3 |
| 5,483,953 | 1/1996 | Cooper | 128/200.22 |
| 5,655,517 | 8/1997 | Coffee . | |

FOREIGN PATENT DOCUMENTS

| | | |
|---|---|---|
| 2008769 | 9/1970 | Germany . |
| 4106564A1 | 9/1992 | Germany . |
| 195704 | 12/1980 | New Zealand . |
| 198774 | 10/1981 | New Zealand . |
| 191545 | 11/1983 | New Zealand . |
| 195704 | 9/1984 | New Zealand . |
| 198774 | 12/1984 | New Zealand . |
| 1005939A | 6/1981 | U.S.S.R. . |
| 1297993 | 11/1972 | United Kingdom . |
| 2018627A | 10/1979 | United Kingdom . |
| 2018627B | 10/1979 | United Kingdom . |
| 1569707 | 6/1980 | United Kingdom . |
| 2 128 900 | 5/1984 | United Kingdom . |
| 2 201 873 | 9/1988 | United Kingdom . |
| WO 91/07232 | 5/1991 | WIPO . |
| WO 92/15339 | 9/1992 | WIPO . |
| WO 93/06937 | 4/1993 | WIPO . |

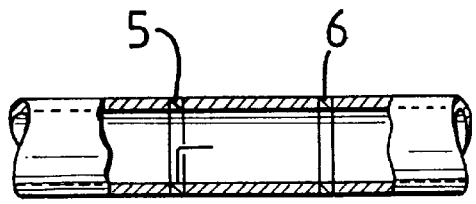
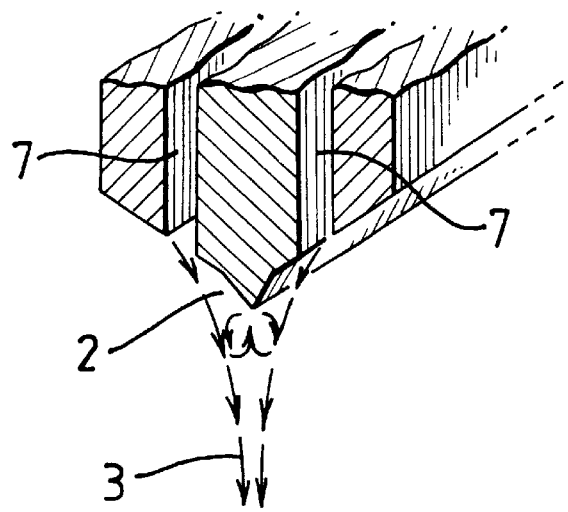
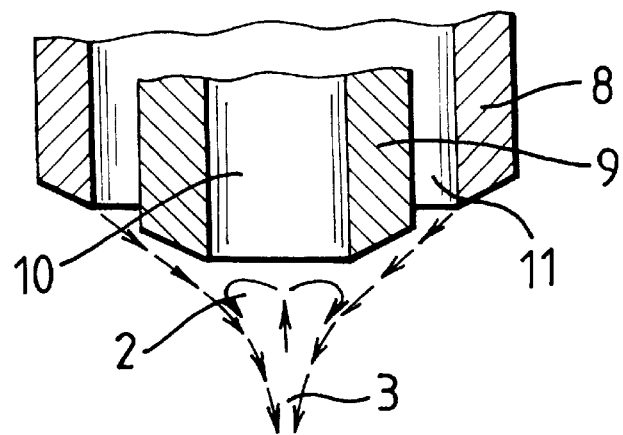

DISPENSING DEVICE

This is a continuation of application Ser. No. 08/456,606 filed Jun. 1, 1995 which is a continuation of PCT application Ser. No. PCT/EP95/01163 filed Mar. 28, 1995 which claimed priority from GB 9406171.0 filed on Mar. 29, 1994.

The invention relates to a dispensing device for comminuting a liquid and the use of such a device, in particular, in medicine.

Known nasal sprays generally produce droplet-sprays by mechanical means. The sprays so produced contain droplets within a broad range of droplet diameters which significantly reduces targeting accuracy and hence accuracy of dosing. The non-uniform nature of the sprays can also be very wasteful of medicament.

Dispensing devices are known which produce a finely divided spray of liquid droplets by electrostatic (more properly referred to as 'electrohydrodynamic') means. The droplet spray in such devices is generated by applying an electric field to a liquid at a spray head or spray edge. The potential of the electric field is sufficiently high to provide comminution of the liquid from the spray head. The droplets produced are electrically charged and thus are prevented from coagulating by mutual repulsion.

United Kingdom patent number 1569707 describes an electrohydrodynamic spray device principally for use in crop spraying. An essential component of the GB 1569707 spray device is a field intensifying electrode, cited adjacent the spray head. The field intensifying electrode is stated to reduce the incidence of corona discharge and allows lower electric field strengths to be used during spray generation.

U.S. Pat. No. 4,801,806 discloses an electrohydrodynamic spray device which produces multiple spray streams.

United Kingdom patent number 2018627B discloses an electrohydrodynamic spray device wherein the droplet spray is fully or partially discharged by means of an earthed electrode having a sharp or pointed edge and located downstream of the spray head. The GB 2018627B spray device does not comprise the field intensifying electrode of GB 1569707.

European Patent number 0234842 discloses an inhaler which uses electrohydrodynamic spray technology. In use, the spray of charged droplets is discharged prior to inhalation by means of a sharp discharge electrode carrying an opposite charge to the droplet spray and located downstream of the spray head. The droplets are discharged so as to target droplet deposition into the lower respiratory tract and to specifically avoid deposition of the droplets onto the mouth and throat of the user.

We have now discovered that electrohydrodynamic spray technology may be used to deliver charged or partially charged monodisperse liquid droplets sprays, especially medicament sprays, to the upper respiratory tract and especially to the nasal mucosa, in an efficient and very controllable manner.

Accordingly, there is provided a device for dispensing a comminuted liquid to the upper respiratory tract, which comprises an electrohydrodynamic comminution means and a means for supplying a liquid to the comminution means.

The electrohydrodynamic comminution means may be any conventional electrohydrodynamic comminution means, for example those described in the above mentioned patent specifications.

Suitably, he comminution means comprises a comminution site, usually a surface or edge and means for electrically charging the liquid at the said site to a potential sufficient to provide comminution of the liquid, the potential usually being of the order of 1–20 kilovolts.

One preferred comminution site is provided by fibres projection from an end surface or edge, the edge or surface being composed susbstantially of fibres.

The surface or edge is conveniently provided by the end surface of a porous bundle of fibres.

A preferred surface or edge is provided by a cone or similar shape.

The fibres are suitably bonded together by a binding means to form the bundle but this is not essential, providing the bundle substantially maintains its shape and provides a suitable surface or edge to allow comminution of the liquid.

A suitable bonding means is a bonding polymer or resin.

Suitably the bundle is shaped into a rod shape, preferably having a cone shaped end which provides the comminution site.

The fibres are generally aligned coaxially within the bundle and are so aligned that liquid flows between the interstitial spaces defined by the fibres to the said comminution site.

It is envisaged that the fibrous comminution site can be used with any type of electrohydrodynamic device such as those disclosed in the above mentioned patent applications and also those disclosed in International Patent Applications, Publication Numbers PCT/GB93/02443 and PCT/GB93/02634. Accordingly, in a further aspect the invention provides a device for comminuting a liquid, which comprises an electrohydrodynamic comminution site, a means for supplying a liquid to the comminution site and a means for electrically charging the comminution site to an electric potential sufficient to comminute the liquid in use, characterized in that the comminution site is provided by fibres projecting from an end surface or edge, the edge or surface being composed substantially of fibres.

Suitable fibres are fibres of ceramic, glass, or polymer such as polyester or nylon. Suitable bundles of fibres are of the types commonly used in fibre tipped pens, an example of which is the Hewlett Packard product number T27847T.

The fibres herein may be of any length or thickness providing they are capable of allowing comminution of the liquid.

Conveniently, the fibrous comminution site is located in a conducting or semi conducting holding means.

A further preferred comminution surface or edge is a thin capillary tube or a slot defined by two parallel plates or concentric cylinders.

The means for supplying a liquid formulation to the comminution means may be any appropriate mechanical or electrical liquid supplying means such as a syringe pump or an electrically powered pump as described in EP 0029301.

Preferably, the communition means is adapted to provide liquid droplets having an average diameter of 10 microns or above, so as to further ensure that the droplets do not enter the lower respiratory tract. Droplets within the range of from 10 to 500 microns in diameter are prarticularly preferred, especially those within the range of from 10 to 200 microns.

For a given liquid the diameter of the charged droplets is suitably controlled by adjustment of the applied comminution voltage and liquid flow rate, using routine experimental procedures.

Liquids having viscosities within the range of from 1 to 500 centipoise and resistivities in the range of from $20^2$–$10^8$ ohm m can be comminuted by the present device.

The device of the invention may be adapted into any embodiment form which dispenses comminuted liquid to the upper respiratory tract, for both medicinal and non-medicinal use.

Preferably, the device is in the form of nasal spray.

A suitable non-medicinal use includes the dispensing of a perfume or an aroma.

A suitable non-medicinal use includes the dispensing of a biocide or an insecticide.

Suitable liquids include liquid medicament formulations or liquid cosmetic formulations such as aroma formulations or perfume formulations.

A preferred liquid is a liquid medicament formulation.

Medicaments suitable for delivery by the device include those used for the treamtment of disorders of the upper respiratory tract including disorders of the nasal mucosa, in particular congestion and disorders of the upper respiratory tract associated with hay fever. Medicaments suitable for delivery by the device also include those used for the treatment of sore throat.

Particular medicaments include nasal decongestants such as oxymetazoline, xylometazoline, phenlephrine, proplyhexadrine, nephazoline and tetrahydrozoline and as appropriate salts thereof such as the hydrochloride salt, and formulations thereof, adapted for administration to the upper respiratory tract.

As described above electrohydrodynamic spray devices are known which produce multiple spray streams. However such devices are not known to be applied to the administration of liquid formulations. Accordingly, there is provided an electrohydrodynamic dispensing device for liquid formulations which comprises a mixing nozzle as described in U.S. Pat. No. 4,802,086.

Thus, by inducing electric field turbulence, two or more liquid components can be mixed at the moment of delivery. This is an essential requirement for ingredients which would react too early if premixed. By reacting too soon before application, they may lose their intended properties or, for example the mixture may increase its viscosity so as to become unsprayable. Such an instantaneous mixing facility at the point and time of application of the mixture has not previously been possible.

Advantageously, the device of the invention, especially when in the form of a nasal spray, also comprises a means to partially electrically discharge the liquid comminution such that the residual charge on the comminution facilitates deposition of the comminution in the upper respiratory tract. The means to partially discharge the comminution is conveniently that disclosed in United Kingdom patent number 2018627B.

When used herein 'medicament' includes proprietary medicines, pharmaceutical medicines and veterinary medicines.

When used herein, unless more specifically defined herein, 'upper respiratory tract' includes the nasal mucosa.

The liquid medicinal formulations for use in the device of the invention may be formulated according to conventional procedures, such as those disclosed in the US Pharmacopoeia, the European Pharmacopoeia, 2nd Edition, Martindale The Extra Pharmacopoeia, 29th Edition, Pharmaceutical Press and the Veterinary Pharmacopoeia.

The liquid cosmetic formulations for use in the device of the invention may be formulated according to conventional procedures, such as those disclosed in Harry's Cosmeticology, 9th Edition, 1982, George Goodwin, London.

SPECIFIC DESCRIPTION OF THE DEVICES AND PROCESSES OF THE INVENTION (1) Comminution sites FIG. 1 shows a thin-walled capillary tube (1), made of conducting, semiconducting or electrically insulating material and electrically connected to a source of high-voltage direct-current, either directly or through the liquid. A single jet (3) is produced from a cusp (2) of liquid, both of which form naturally, according to the voltage and flow rate for a given liquid. FIG. 2 shows a conducting, semiconducting or insulating cylinder (1) which may have a larger diameter than those shown in FIG. 1. This nozzle has an inner-member, (4) which is approximately coaxial with the outer tube, (1). FIG. 3 shows a slot nozzle, formed between two parallel plates (2) having conducting, semiconducting or insulating edges electrically connected to a high-voltage direct-current supply, from which the liquid emerges, forming cusps and jets when the voltage supply and liquid flow rates are suitably adjusted according to the type of liquid being sprayed. For a given jet (and thus droplet) size, and a given liquid, this nozzle may enable a higher flow rate to be achieved than those in which a single cusp and jet are used.

FIG. 7 shows a fibre tipped comminution site or nozzle (12) comprising a porous bundle of resin bonded fibres having a pointed tip (13). The bundle is held in an electrically conducting or semi conducting base (14) which also comprises a hollowed portion (15) forming a reservoir for the liquid. The liquid flows from the reservoir (15) to the base (16) of the fibre tipped bundle and thereafter flows through the bundle to the pointed tip (13).

The bundle is connected to a high voltage source, through the conducting or semi conducting base (14) or the bundle may be earthed through the base in the presence of an adjacent high voltage source, so as to create a high electric field at the pointed tip (13). When the voltage is applied the liquid at the pointed tip (13) forms into an electrohydrodynamic jet which subsequently breaks up, thus providing a spray of charged droplets.

(2) Flow Inducers

An example of such a device is that illustrated in FIG. 4 which shows an ion stream flow inducer, wherein a high voltage electrode (5) breaks up pairs of charge carriers within the liquid, thus neutralizing those of opposite polarity at the electrode, and leaving a large population of monionized like-polarity charge carriers which stream away from the high voltage electrode by coulombic force, thus moving the liquid in the direction of the counter electrode (6) by means of viscous drag. This pumping means requires that an electrode (5) is able to effectively inject like-polarity charge carriers into the liquid, close to the electrode (5). This may be effectively done by used a sharp-edge conducting or semiconducting surface, held at a sufficiently high potential to disrupt lightly bonded charge carriers or to ionize the liquid. Normally, it is only possible to establish a strong enough field for both creating unipolar charge carriers and pumping the liquid, when the liquid is of sufficient resistivity. Typically a resistivity of, say 10 (exp. 8) ohm meters, will pump at several milliliter per minute, with a head of up to one meter, at a voltage of 10 to 20 kilovolts, and a direct current of only a few microamperes. More conductive liquids will draw more current and will establish a weaker electric field. Thus highly conducting liquids, such as, say tap water may not readily establish a practicable drag pressure.

(3) Reactive Liquid Mixing

Two or more liquids may be mixed after emerging from the nozzle by maximizing turbulent motion which can be induced with the cusp (2) which forms the base of each liquid jet (3). FIG. 5 shows a nozzle formed by three parallel plates, forming two slot-gaps (7) through which two liquids, a and b, are induced to flow, and to subsequently become mixed in the cone-shaped liquid base (2) of each jet, in accordance with eddy currents that can be induced as shown.

This mixing may be maximized by using a liquid formulation having the lowest possible viscosity for each liquid; the maximum nozzle potential; and an optimal flow rate and degree of asymmetry of the individual flow rates of the component liquids.

An alternative to the mixing arrangement of FIG. 5 is shown in cross section in FIG. 6, in which two coaxial cylinders (8) and (9) form two flow-channels (13) and (11). This arrangement has advantages and may induce a greater degree of mixing in some cases, for example, when there is a significant disparity in the flow rates of liquids a and b.

I claim:

1. A method of dispensing comminuted matter to the upper respiratory tract, which comprises: supplying liquid to a liquid outlet nozzle comprising a porous bundle of resin bonded fibres forming a cone shape ending in a pointed tip; and creating a high electric field at the pointed tip by coupling an electrical potential to the bundle causing liquid at the pointed tip to form an electrohydrodynamic jet which breaks up into a spray of electrically charged droplets for supply to the upper respiratory tract.

2. A method of dispensing comminuted matter to the upper respiratory tract, which comprises supplying liquid to a liquid outlet nozzle in the form of a cone shaped fibre bundle ending a tip and comprising fibres selected from the group consisting of ceramic, glass, polyester and nylon fibres and creating a high electric field at the tip by coupling an electrical potential to the bundle causing liquid at the pointed tip to form an electrohydrodynamic jet which breaks up into a spray of electrically charged droplets from supply to the upper respiratory tract.

3. A method of treating nasal congestion, which comprises: supplying liquid containing a nasal decongestant selected from the group consisting oxymetazoline xylometazoline, phenylephrine, propylhexadrine, nephazoline, tetraphydrozoline and appropriate salts thereof to a liquid outlet nozzle comprising a bundle of fibres forming a cone shape ending in a tip; and creating a high electric field at the tip by coupling an electrical potential to the bundle causing liquid at the tip to form an electrohydrodyhamic jet which breaks up into a spray of charged droplets for supply to the upper respiratory tract.

4. A method of dispensing comminuted liquid to the upper respiratory tract, which comprises: supplying liquid to a liquid outlet nozzle comprising a porous bundle of fibres forming a cone shape ending in a tip; creating a high electric field at the tip by coupling an electrical potential to the bundle causing liquid at the tip to form an electrohydrodynamic jet which breaks up into a spray of charged droplets; and at least partially electrically discharging the charged droplets before supply to the upper respiratory tract.

5. A method of dispensing comminuted liquid to the upper respiratory tract, which comprises: supplying liquid to a liquid outlet nozzle comprising fibres selected from the group consisting of ceramic glass, polyester and nylon fibres and arranged to form a cone shaped fibre bundle ending in a tip; creating a high electric field at the tip by coupling an electrical potential to the bundle causing liquid at the tip to form an electrohydrodynamic jet which breaks up into a spray of charged droplets and at least partially electrically discharging the charged droplets before supply to the upper respiratory tract.

6. A method according to any one of claims 1 to 5, which comprises creating the electrical field so that the charged droplets have an average diameter of at least 10 microns.

7. A method according to any one of claims 1 to 5, which comprises creating the electrical field so that the charged droplets have an average diameter in the range of 100 to 500 microns.

8. A method of treating nasal congestion which comprises supplying liquid containing a nasal decongestant selected from the group consisting oxymetazoline, xylometazoline, phenylephrine, propylexadrine, nephazoline, tetrahydrozoline and appropriate salts thereof to a liquid outlet nozzle comprising fibres selected from the group consisting of ceramic, glass, polyester and nylon fibres and forming a cone shaped fibre bundle ending in a pointed tip; creating a high electric field at the tip by coupling an electrical potential to the bundle causing liquid at the pointed tip to form an electrohydrodynamic jet which breaks up into a spray of charged droplets having an average diameter of at least 10 microns; and at least partially electrically discharging the charged droplets before supply to the upper respiratory tract.

9. An inhaler comprising: a liquid supplier having a liquid outlet nozzle comprising a porous bundle of fibres forming a cone shape ending in a pointed tip; and an electric charger for creating a high electric field at the pointed tip by coupling an electrical potential to the bundle causing liquid at the pointed tip to form an electrohydrodynamic jet which breaks up into a spray of charged droplets for supply to the upper respiratory tract.

10. An inhaler comprising: a liquid supply having a liquid outlet nozzle comprising fibres selected from the group consisting of ceramic, glass, polyester and nylon fibres and arranged to form a cone shaped fibre bundle ending in a tip; and an electric charger for creating a high electric field at the tip by coupling an electrical potential to the bundle to cause liquid at the tip to form an electrohydrodynamic jet which beaks up into a spray of charged droplets for supply to the upper respiratory tract.

11. An inhaler comprising a liquid supplier having a liquid outlet nozzle comprising a porous bundle of fibres forming a cone shape ending in a tip; an electric charger for creating a high electric field at the tip by coupling an electrical potential to the bundle to case liquid at the tip to form an electrohydrodynamic jet which breaks up into a spray of charged droplets; and an electrical discharger for at least partially electrically discharging the charged droplets before supply to the upper respiratory tract.

12. An inhaler comprising: a liquid supplier having a liquid outlet nozzle comprising an electrically conducting or semi-conducting base defining a reservoir for liquid and a bundle of fibres held in the base, the bundle of fibres having a cone shape ending in a tip; and an electric charger for creating a high electrical field at the tip by coupling an electrical potential to the base to cause liquid at the tip to break up into a spray of charged droplets for supply to the upper respiratory tract.

13. An inhaler comprising: a liquid supplier having an electrically conducting or semi-conducting base defining a reservoir for liquid and a bundle of fibres held in the base, the bundle of fibres having a cone shape ending in a pointed tip and being formed of fibres selected from the group consisting of ceramic, glass, polyester and nylon fibres; an electric charger for creating a high electric field at the tip by coupling an electrical potential to the base to cause liquid at the tip to form an electrohydrodynamic jet that breaks up into a spray of electrically charged droplets having an average diameter of at least 10 microns; and an electrical discharger for at least partially electrically discharging the charger droplets before supply to he upper respiratory tract.

14. An inhaler according to any one of claims 9 to 13, further comprising an ion stream flow inducer for causing liquid to flow to the liquid outlet nozzle, which ion stream flow inducer has an electrode for receiving a high voltage to cause pairs of charger carriers within the liquid to break up to neutralise charge carriers of opposite polarity at the ion flow inducer electrode thereby leaving a larger population of like-polarity charge carriers which stream away from the ion stream inducer electrode towards the liquid outlet nozzle and which cause the liquid to move in the same direction by virtue of viscous drag.

* * * * *